(12) United States Patent
Kawahara et al.

(10) Patent No.: US 6,723,704 B2
(45) Date of Patent: Apr. 20, 2004

(54) SPHINGOGLYCOLIPID

(75) Inventors: Kazuyoshi Kawahara, Tokyo (JP); Katsumi Murata, Tokyo (JP)

(73) Assignees: Kibun Food Chemifa Co., Ltd., Tokyo (JP); The Kitasato Institute, Tokyo (JP)

( * ) Notice: Subject to any disclaimer, the term of this patent is extended or adjusted under 35 U.S.C. 154(b) by 20 days.

(21) Appl. No.: 09/894,140

(22) Filed: Jun. 29, 2001

(65) Prior Publication Data

US 2002/0037291 A1 Mar. 28, 2002

(30) Foreign Application Priority Data

Jun. 29, 2000 (JP) .......................... 2000-196204

(51) Int. Cl.⁷ .................. A61K 31/702; C07H 3/06
(52) U.S. Cl. .................. 514/25; 514/53; 514/54; 514/61; 514/62; 536/4.1; 536/17.2; 536/123.1; 536/123.13
(58) Field of Search .................. 514/25, 62, 53, 514/54, 61; 536/4.1, 53, 17.2, 123.1, 123.13

(56) References Cited

U.S. PATENT DOCUMENTS

| 5,672,693 A | 9/1997 | Kawahara |
| 5,679,357 A | 10/1997 | Dubief et al. |
| 5,700,456 A | 12/1997 | Dubief et al. |

FOREIGN PATENT DOCUMENTS

| EP | 0 587 288 | 3/1994 |
| EP | 0 639 580 | 2/1995 |
| EP | 0 669 430 | 3/1996 |
| EP | 0 887 070 | * 12/1998 |
| EP | 0 978 274 | 2/2000 |
| JP | 61286307 | 12/1986 |
| JP | 06080007 | 8/1987 |
| JP | 62-187404 | 8/1987 |
| JP | 01242690 | 9/1989 |
| JP | 02048520 | 2/1990 |
| JP | 04159203 | 6/1992 |
| JP | 05039485 | 2/1993 |
| JP | 06157283 | 6/1994 |
| JP | 07133217 | 5/1995 |
| JP | 07285827 | 10/1995 |
| JP | 11043437 | 2/1999 |
| WO | WO 97/15274 | 5/1997 |

OTHER PUBLICATIONS

Akihiro Yamamoto et al., "Isolation of a Novel Sphingoglycolipid Containing Glucuronic Acid and 2–Hydroxy Fatty Acid from *Flavobacterium devorans* ATCC 10829", *J. Biochem.*, 1978, pp. 1213–1216, vol. 83.

Eiko Yabuuchi et al., "*Flavobacterium Devornas* ATCC 10829: A Strain of *Pseudomonas Paucimobilis*", *J. Gen. Appl. Microbiol.*, 1979, pp. 95–107, vol. 25.

Kazuyoshi Kawahara et al., "Isolation of an Unusual "Lipid A" Type Glycolipid from *Pseudomonas Paucimobilis*", *Biochimica et Biophysica Acta*, 1982, pp. 571–575, vol. 712.

Eiko Yabuuchi et al., "Proposals of *Sphingomonas paucimobilis* gen. nov. and comb. nov., *Sphingomonas parapaucimobilis* sp. nov., *Sphingomonas yanoikuyae* sp. nov., *Sphingomonas adhaesiva* sp. nov., *Sphingomonas capsulata* comb. nov., and Two Genospecies of the Genus *Sphingomonas*", *Microbiol. Immunol.*, 1990, pp. 99–119, vol. 34 (2).

* cited by examiner

Primary Examiner—James O. Wilson
Assistant Examiner—Leigh C. Maier
(74) Attorney, Agent, or Firm—Browdy and Neimark, P.L.L.C.

(57) ABSTRACT

A glycosphingolipid having a sugar chain containing α-glucosamine and β-glucosamine is disclosed. Such glycosphingolipid is advantageous in that possibly being manufactured in a facile and inexpensive manner, and that exhibiting moisturizing effect and immuno-enhancing activity.

11 Claims, 1 Drawing Sheet

Fig.1

SPHINGOGLYCOLIPID

FIELD OF THE INVENTION

The present invention relates to a novel glycosphingolipid and applications thereof, and more specifically to a novel glycosphingolipid having a characteristic structure in the sugar portion thereof, and its applications as cosmetics and pharmaceuticals.

RELATED ART

Rough skin is caused by excessive loss of moisture from the surface of the skin exposed to dry air or cleansing. In these days, various environmental chemical substances may also inhibit skin functions such as lipid secretion, which results in rough skin. Therefore, there is a demand for providing a substance capable of preventing rough skin and having an excellent moisturizing effect.

Various active compounds having a moisturizing effect have been provided, which mainly comprise water-soluble polyols. Some of them including propylene glycols have already been commercialized. However, many of commercialized moisturizing compounds are associated with uncomfortable feel when they are applied or only available with insufficient moisturizing effect, so that there is still a strong demand for the development of a new moisturizing compound.

In such situation, glycosphingolipid attracts a great deal of attention as a safe moisturizing compound.

For example, Japanese Laid-Open Patent Publication Nos. 1-242690, 2-48520 and 4-159203, and Japanese Examined Patent Publication No. 6-80007 describe that glycosphingolipid has skin moisturizing effect. Japanese Laid-Open Patent Publication No. 6-157283 discloses a skin moisturizing cosmetic for external use containing as one ingredient a glycosphingolipid expressed by a specific general formula. Details of the structures of such glycosphingolipids disclosed in the foregoing publications have, however, been not clear.

Japanese Laid-Open Patent Publication No. 61-286307 is one literature specifically defines a glycosphingolipid having moisturizing effect. The publication describes that ganglioside has skin moisturizing effect and emollient effect, and discloses a skin cosmetic containing ganglioside and a salt thereof. Ganglioside is a kind of glycosphingolipid containing amino sugars and sialic acid besides neutral sugars.

Japanese Laid-Open Patent Publication Nos. 5-39485, 7-133217 and 7-285827 disclose skin agents for external use containing cerebroside. Cerebroside is a kind of glycosphingolipid comprising each one mol of fatty acid, sphingosine base and neutral sugar (galactose or glucose).

Japanese Laid-Open Patent Publication No. 11-43437 describes that a glycosphingolipid having a specific structure has moisturizing effect, whose sugar chain is limited to that containing 1 to 4 hexoses selected from the group comprising uronic acid, glucosamine, galactose and mannose, as combined with one uronic acid.

As has been described in the above, while several kinds of structures have been defined as for glycosphingolipid having moisturizing effect, there is still a need for providing a novel glycosphingolipid having a novel structure. In particular, most strong need resides in that providing a novel glycosphingolipid having moisturizing effect and other miscellaneous activities, and is possibly be manufactured in a relatively facile manner.

Considering such prior art, it is therefore an object of the present invention to provide a glycosphingolipid having a novel structure, and more particularly to provide a glycosphingolipid having moisturizing effect and other miscellaneous activities, and is possibly be manufactured in a relatively facile manner.

SUMMARY OF THE INVENTION

The present inventors found out that a novel glycosphingolipid is contained in components of a somatic extract from bacterium Sphingomonas sp., which led us to complete the present invention.

That is, the present invention provides a glycosphingolipid having a sugar chain containing α-glucosamine and β-glucosamine.

The sugar chain preferably comprises mannose, β-glucosamine, α-glucosamine and glucuronic acid, and more preferably has a structure expressed by formula (A) below:

$$\alpha\text{-Man-}(1\rightarrow3)\text{-}\beta\text{-GlcN-}(1\rightarrow6)\text{-}\alpha\text{-GlcN-}(1\rightarrow4)\text{-}\alpha\text{-GlcA} \quad (A)$$

(where, Man represents mannose, GlcN represents glucosamine and GlcA represents glucuronic acid).

The glycosphingolipid of the present invention is particularly preferable if it has a structure expressed by the formula below:

(I)

(where, $R^1$ represents the sugar chain containing α-glucosamine and β-glucosamine, $R^2$ represents any one of an alkyl group possibly having cycloalkyl group, an alkenyl group and an alkynyl group; $R^3$ represents an alkyl group; all of such alkyl group, alkenyl group and alkynyl group may be straight or branched, and may be substituted or unsubstituted).

$R^2$ preferably has a carbon number of 15 to 25, and more preferably has a structure expressed by any one of the formulae below. It should now be noted that a numerical range expressed with a word "to" in this specification includes both end values as a minimum value and a maximum value, respectively.

$R^3$ is preferably a substituted or unsubstituted straight alkyl group having a carbon number of 10 to 20, and more preferably a straight alkyl group having a carbon number of 12.

The present invention also provides a cosmetic and a pharmaceutical composition containing such glycosphingolipid, in particular a moisturizer and an immuno-enhancer.

BRIEF DESCRIPTION OF THE DRAWINGS

The above and other objects, features and advantages of the present invention will become more apparent from the following description of the presently preferred exemplary embodiment of the invention taken in conjunction with the accompanying drawing, in which.

DETAILED DESCRIPTION OF THE INVENTION

The glycosphingolipid of the present invention and applications thereof will be detailed hereinafter.

The glycosphingolipid of the present invention is characterized in that the sugar chain thereof contains α-glucosamine and α-glucosamine. The sugar chain may be composed only of α-glucosamine and β-glucosamine, or may contain other sugars. In any case, the number of α-glucosamine and β-glucosamine units contained in one molecule of the sugar chain, order of the arrangement thereof and the bonding style are not specifically limited. There is no specific limitation also on the species of the sugars other than α-glucosamine and β-glucosamine, and possible examples thereof include uronic acid, galactose, mannose and glucuronic acid.

A preferable glycosphingolipid of the present invention is such that having a sugar chain containing 1 mol each of α-glucosamine and β-glucosamine. A more preferable glycosphingolipid is such that having a tetrasaccharide chain comprising a mannose, a β-glucosamine, an α-glucosamine and a glucuronic acid, and still more preferable one is such that having a sugar chain expressed by the foregoing formula (A).

The glycosphingolipid of the present invention is preferably such that having a structure expressed by the foregoing formula (I).

$R^1$ in formula (I) represents the sugar chain containing α-glucosamine and β-glucosamine, where preferable ranges thereof are as described already in the above.

$R^2$ in formula (I) represents any one of an alkyl group possibly having cycloalkyl group, an alkenyl group and an alkynyl group; any of which may be straight or branched, and may be substituted or unsubstituted. While there is no specific limitation on the carbon number of $R^2$, it preferably resides in a range from 15 to 25. The alkyl group, alkenyl group and alkynyl group expressed by $R^2$ may be straight or branched, and may be substituted typically with a hydroxyl group or unsubstituted. In particular the alkyl group may have a cycloalkyl group such as a cyclopropyl group contained therein. The positions of a double bond in the alkenyl group and a triple bond in the alkynyl group are not specifically limited.

Specific structures for $R^2$ can be exemplified as those expressed by the foregoing structures "a" to "c".

$R^3$ in formula (I) represents an alkyl group. The alkyl group allowed for $R^3$ may be straight or branched, and may be substituted typically with a hydroxyl group or unsubstituted. The carbon number of the alkyl group is generally within a range from 1 to 50, and preferably within a range from 15 to 25. A specific example for $R^3$ can be exemplified as a straight alkyl group having a carbon number of 12.

Preferable and specific examples of the glycosphingolipid expressed by formula (I) may be a compound in which $R^1$ is a sugar chain expressed by formula (A), $R^2$ is a group having any one of the structures "a" to "c", and $R^3$ is a straight alkyl group having a carbon number of 12.

The glycosphingolipid of the present invention can be obtained by extracting it from somatic body containing such compound. Since the glycosphingolipid is contained in somatic body of bacteria Sphingomonas sp., extraction from either bacteria of Sphingomonas sp. will successfully yield the glycosphingolipid of the present invention. In particular, an easy extraction is expectable from Sphingomonas sp. MK346 (IAM14824).

Since the glycosphingolipid of the present invention is insoluble to acetone, it is preferable to wash the bacterial cells with acetone prior to the extraction. Solvent for extracting the glycosphingolipid of the present invention is preferably an alcoholic solvent such as methanol, or a mixed solvent of an alcoholic solvent and a polar solvent such as chloroform in terms of the yield ratio. Any other solvents are also allowable so far as they can dissolve the glycosphingolipid.

For the case that the glycosphingolipid is obtained as a mixture, the individual components can be isolated by a technique, such as chromatography, well known to those skilled in the art. The chromatographic conditions including a column-packing material, eluent, elution rate, pressure and temperature can properly be selected. It is also allowable to react a reagent selectively reactive with a specific substance contained in the mixture of the glycosphingolipid to thereby obtain a derivative of such substance, which is then isolated based on chemical or physical property thereof. Details of the specific procedures for the isolation will be explained later in Examples.

The glycosphingolipid of the present invention can also be synthesized by a combination of known synthetic procedures. A typical case relates to that the sugar portion and the sphingosine portion are separately synthesized or extracted from bacterial cells in advance and such portions are then bound with an amide bond to thereby produce glycosphingolipid of the present invention. Such preparation partially relying upon the synthetic method, however, is generally associated with some difficulty as compared with the full extraction from the bacterial cells, so that it is preferable to choose the full extraction from the bacterial cells.

The glycosphingolipid of the present invention is highly versatile, and typically exhibits moisturizing effect and immuno-enhancing activity, which allows the glycosphingolipid of the present invention to be used for cosmetic, pharmaceutical composition and so forth.

There is no special limitation on the forms of the cosmetic or pharmaceutical composition containing the glycosphingolipid of the present invention, so that any forms of solid, liquid, paste, jelly and powder are allowable. To accomplish such forms, it is allowable to use a gelling agent for solidification, or to use a liquid for dispersion. It is still also allowable to add a solvent for solubilization, or to pulverize by stray drying.

For example, the cosmetic or the pharmaceutical composition of the present invention is available as toilet soaps, shampoos, face washes, rinses, eye creams, eye shadows, creams and/or emulsions, lotions, perfumes, face powders, cosmetic oils, cosmetic products for hair and scalp, hair dyes, solid perfumes, powders, packs, shaving creams, shaving lotions, suntan oils, sunscreen oils, suntan lotions, sunscreen lotions, suntan creams, sunscreen creams, foundations, powder perfumes, cheek colors, mascaras, eyebrow colors, nail creams, nail enamels, nail enamel removers, hair washes, bath cosmetics, lip colors, lip creams, eyeliners, dentifrices, deodorant products, eaux de cologne, hair growers, etc. The cosmetic or the pharmaceutical composition of the present invention is also available as ointments or fomentations.

The cosmetic or the pharmaceutical composition of the present invention may also contain various ingredients other than the glycosphingolipids depending on the purpose of use such as improvement in emollient effect, improvement in feel of use, moderation of dehydration after use, improvement in solubility, improvement in emulsifiability, improvement in emulsification stability, improvement in compatibility with oily ingredients, moderation of feel of stretch after use, improvement in dermal affinity, improvement in spreadability on the skin, moderation of greasiness, prevention of rough skin, enhancement of whitening effect, improvement in skin-protecting effect, keratin improvement, normalization of epidermal keratinization (prevention of parakeratosis, prevention of acanthosis and inhibition of disorder of epidermal lipid metabolism due to promoted turnover of the skin), moderation of xeroderma such as senile xeroderma, improvement in rough skin conditions such as crack or desquamation, inhibition of the formation of wrinkles, removal of wrinkles, wound healing, prevention and improvement in pigmentation, antiaging, moderation of dandruff or itch, moderation of loss of hair, prevention and treatment of scalp diseases, improvement in storability, improvement in softness, improvement in elasticity, glossing, suppression of melanogenesis, and prevention of sunburn.

Depending on the purpose of use, the cosmetic or the pharmaceutical composition of the present invention may appropriately contain other ingredients such as fats and oils, phospholipids, UV absorbers, IR absorbers, emulsifiers, surfactants, preservatives, antifungal agents, antioxidants, whitening agents, vitamins, amino acids, hormones, peptides, bioactive plant extracts, fluorescent materials, pigments, dyes, perfumes, scrubbing agents, sequestrants, binders, extenders, thickeners, sugars, nutrient ingredients, pH modulators, chelating agents, antibacterials, keratin improvers, keratolytic agents, antibiotics, skin penetration enhancers, blood circulation promoters, antiphlogistics, cytotonic agents, antiinflammatory agents, analgesics, skin softeners, emollients, wound healing agents, metabolism enhancers, etc. Additional moisturizing ingredients other than glycosphingolipids expressed by formula (I) may also be contained.

Suitable fats and oils for use in the cosmetic or the pharmaceutical composition of the present invention include fatty acids such as oleic acid, behenic acid, isostearic acid, lauric acid, myristic acid, palmitic acid, stearic acid, linolic acid, γ-linolenic acid, columbic acid, eicosa-(n-6,9,13)-trienoic acid, arachidonic acid, α-linolenic acid, tymnodonic acid, hexaenoic acid; ester oils such as pentaerythritol-tetra-2-ethyl hexanoate, isopropyl myristate, butyl stearate, hexyl laurate, octyldodecyl myristate, diisopropyl adipate, diisopropyl sebacate; waxes such as beeswax, spermaceti, lanolin, carnauba wax, candelilla wax, vaseline; animal and plant oils such as mink oil, olive oil, castor oil, cacao butter, palm oil, cod liver oil, beef tallow, butter fat, evening primrose oil, rice bran oil, squalane; mineral oils such as hydrocarbon oils, liquid paraffin; silicone oils such as methyl phenyl silicone, dimethyl silicone; higher alcohols such as lauryl alcohol, stearyl alcohol, oleyl alcohol, cetyl alcohol, 2-octyl dodecanol, 2-decyl tetradecanol and derivatives thereof. Suitable organic acids include α-hydroxy acid, hydroxycarboxylic acid, dicarboxylic acid, glycyrrhizic acid, glycyrrhetic acid, mevalonic acid (mevalolactone).

Suitable phospholipids for use in the cosmetic or the pharmaceutical composition of the present invention include monoacylester-type glycerophospholipids and diacylester-type glycerophospholipids. Specific examples include lysophosphatidylcholine, lysophosphatidylethanolamine, lysophosphatidylserine, lysophosphatidylinositol, phosphatidylcholine, phosphatidylethanolamine, phosphatidylinositol, phosphatidylserine, phosphatidylglycerol, phosphatidic acid and sphingomyelin. Naturally occurring lecithins such as yolk, and hydrogenates of the compounds mentioned above may also be used.

Suitable UV absorbers for use in the cosmetic or the pharmaceutical composition of the present invention include oxybenzone (2-hydroxy-4-methoxybenzophenone), oxybenzonesulfonic acid, oxybenzonesulfonic acid (trihydrate), guaiazulene, ethylene glycol salicylate, octyl salicylate, dipropylene glycol salicylate, phenyl salicylate, homomenthyl salicylate, methyl salicylate, methyl diisopropylcinnamate, cinoxate (2-ethoxyethyl p-methoxycinnamate), glyceryl di-p-methoxycinnamate mono-2-ethylhexylate, 2,2'-dihydroxy-4-methoxybenzophenone, sodium 2,2'-dihydroxy-4-methoxybenzophenone-5,5'-disulfonate, 2,4-dihydroxybenzophenone, 2,3,4,4'-tetrahydroxybenzophenone, p-aminobenzoic acid, ethyl p-aminobenzoate, glyceryl p-aminobenzoate, amyl p-dimethylaminobenzoate, 2-ethylhexyl p-dimethylaminobenzoate, p-hydroxyanisol, 2-ethylhexyl p-methoxycinnamate, isopropyl p-methoxycinnamate, diisopropyl cinnamate ester, 2-(2-hydroxy-5-methylphenyl) benzotriazole, sodium 2-hydroxy-4-methoxybenzophenone-5-sulfonate, 4-tert-butyl-4'-methoxybenzoylmethane, 2-ethylhexyl salicylate, glyceryl p-monobenzoate, methyl orthoaminobenzoate, 2-hydroxy-4-methoxybenzophenone, amyl p-dimethylaminobenzoate, 2-phenylbenzimidazol-5-sulfonic acid, 2-hydroxy-4-methoxybenzophenone-5-sulfonic acid, dicaproyl trioleate, 2-ethoxyethyl p-methoxycinnamate, butylmethoxy-benzoylmethane, glyceryl mono-2-ethylhexanoyl-di-p-methoxybenzophenone, 2-ethylhexyl-2-cyano-3,3'-diphenylacrylate, 2,2'-dihydroxy-4-methoxybenzophenone and ethyl 4-bishydroxypropyl aminobenzoate.

Suitable emulsifiers and surfactants for use in the cosmetic or the pharmaceutical composition of the present invention include nonionic surfactants, anionic surfactants and cationic surfactants.

Examples of nonionic surfactants include sorbitan esters such as sorbitan monolaurate, sorbitan monooleate, sorbitan monoisostearate; polyoxyethylene sorbitan esters such as polyoxyethylene sorbitan monoisostearate, polyoxyethylene sorbitan monolaurate, polyoxyethylene sorbitan monooleate; glycerol ethers such as glycerol monoisostearate, glycerol monomyristate; polyoxyethylene glycerol ethers such as polyoxyethylene glycerol monoisostearate, polyoxyethylene glycerol monomyristate; polyglycerin fatty acid esters such as diglyceryl monostearate, decaglyceryl decaisostearate, diglyceryl diisostearate; glycerin fatty acid esters such as glyceryl monocaprate, glyceryl monolaurate, glyceryl monomyristate, glyceryl monopalminate, glyceryl monooleate, glyceryl monostearate, glyceryl monolinoleate, glyceryl monoisostearate, glyceryl monodilinoleate, glyceryl monodicaprate; polyoxyethylene glycerin fatty acid esters such as polyoxyethylene glyceryl monomyristate, polyoxyethylene glyceryl monooleate, polyoxyethylene glyceryl monostearate; polyoxyethylene branched alkyl ethers such as polyoxyethylene octyldodecyl alcohol, polyoxyethylene-2-decyltetradecyl alcohol; polyoxyethylene alkyl ethers such as polyoxyethylene oleyl alcohol ether, polyoxyethylene cetyl alcohol ether; polyoxyethylene hydrogenated castor oil fatty acid esters such as polyoxyethylene hydrogenated castor oil, polyoxyethylene dihydrocholesterol ether, polyoxyethylene hydrogenated castor oil isostearate; and polyoxyethylene alkyl aryl ethers such as polyoxyethylene octyl phenol ether.

Examples of anionic surfactants include salts of higher fatty acids such as oleic acid, stearic acid, isostearic acid, palmitic acid, myristic acid, behenic acid, for example, diethanolamine salts, triethanolamine salts, amino acid salts, potassium salts and sodium salts; ether carboxylic acid alkali salts; N-acylamino acid salts; N-acyl sarcosinates; and higher alkyl sulfonates. Examples of cationic surfactants include alkyl quaternary ammonium salts, polyamines and alkyl amine salts.

Suitable powders for use in the cosmetic or the pharmaceutical composition of the present invention include talc, kaolin, fuller earth, gum, starch, silica, silicic acid, aluminum silicate hydrate, chemically modified aluminum magnesium silicate, sodium polyacrylate, tetraalkyl aryl ammonium smectite, trialkyl aryl ammonium smectite, ethylene glycol monostearate, sodium carboxymethylcellulose, carboxyvinyl polymers, chalk, gummy matters, ethylene glycol monostearate and ethylene glycol distearate.

Suitable polyols for use in the cosmetic or the pharmaceutical composition of the present invention include glycerin, polyglycerins (such as diglycerin, triglycerin, tetraglycerin), ethylene glycol, propylene glycol, 1,3-butylene glycol, 1,4-butylene glycol, dipropylene glycol, polyethylene glycol, sorbitol, erythritol, maltotriose, threitol, sucrose, glucose, maltose, multitose, fructose and xylitose.

Other materials suitable for use in the cosmetic or the pharmaceutical composition of the present invention include vitamins such as vitamin A, vitamin $B_1$, vitamin $B_2$, vitamin $B_6$, vitamin $B_{12}$, vitamin C, vitamin D, vitamin E and vitamin K; amino acids such as proline, leucine, isoleucine, alanine, threonine, lysine, cysteine and arginine; hormones such as estrogen, pregnenolone and adrenocortical hormone; peptides such as keratin, collagen and elastin; sugars as listed above for polyols; inorganic salts such as sodium chloride, sodium hydrogencarbonate, sodium carbonate, borax, sodium sulfate, sodium sulfide, sodium thiosulfate, sodium sesquicarbonate, magnesium oxide, calcium carbonate, magnesium carbonate, potassium chloride and potassium sulfide; *Streptococcus themophilus* cultures; sterols such as cholesterol, provitamin $D_3$, campesterol, stigmastanol, stigmasterol, 5-dihydrocholesterol, α-spinastenol and cholesterol fatty acid esters; sphingosines such as sphingosine, dihydrosphingosine, phytosphingosine, dehydrosphingosine, dehydrophytosphingosine and sphingadienine; ceramides; pseudoceramides; saponins; chitin derivatives; oligosaccharides such as maltose, xylobiose, isomaltose, lactose, sucrose, raffinose, maltotriose, xylotriose, maltotetraose, xylotetraose, maltopentaose, xylopentaose, maltohexaose, xylohexaose, maltoheptaose and xyloheptaose; acid mucopolysaccharides such as hyaluronic acid, chondroitin sulfate, dermatan sulfate, heparin and heparan sulfate; and yeast extracts.

The cosmetic or the pharmaceutical composition of the present invention may further contain thickeners such as carboxyvinyl polymers, carboxymethylcellulose, polyvinyl alcohol, xanthan gum, carrageenan, alginates, propylene glycol alginate esters and gelatin; electrolytes such as sodium chloride; whitening agents such as arbutin, allantoin, vitamin E derivatives, glycyrrhizin, magnesium ascorbyl phosphate, kojic acid, pantothenic acid derivatives, placenta extract, coix seed extract, green tee, kudzu root, mulberry root, glycyrrhiza, scutellaria root, aloe, orange peel, chamomile and Ganoderma lucidum; skin protective agents such as retinol, retinol esters and retinoic acid; skin softeners such as stearyl alcohol, glyceryl monoricinoleate, mink oil, cetyl alcohol, stearic acid, coconut oil, castor oil and isostearic acid; emollients such as stearyl alcohol, glycerin monoricinoleate, glycerin monostearate and cetyl alcohol; skin penetration enhancers such as 2-methylpropane-2-ol, 2-propanol, ethyl 2-hydroxypropionate, 2,5-hexanediol, acetone and tetrahydrofuran; bioactive plant extracts such as aloe, arnica, glycyrrhiza, sage and swertia herb extracts; preservatives such as p-hydroxybenzoate esters, sodium benzoate, urea, methylparaben, ethylparaben, propylparaben and butylparaben; antiinflammatory agents such as salicylic acid; germicides such as triclosan; antioxidants such as α-tocopherol and butylhydroxytoluene; buffers such as triethanolamine or a combination of sodium hydroxide and lactic acid; keratolytic agents such as lactic acid, glycolic acid, malic acid, tartaric acid and citric acid; scrubbing agents such as polyethylene powder; pigments such as calcium, barium or aluminum lake, iron oxide, titanium dioxide and mica.

The cosmetic or pharmaceutical composition of the present invention may also contain other materials depending on the purpose of use. The amount of each ingredient to be added and the method for adding it can be determined by those skilled in the art.

The amount of use of the cosmetic or pharmaceutical composition can properly be determined within a range so far as desired effects will fully be exhibited.

Next paragraphs will describe the present invention in more detail referring to preferable Examples. It should now be noted that the materials, amount of use thereof, ratio, details for the processes, processing procedures or so may properly be modified without departing from the spirit of the present invention. The present invention is thus by no means limited to the specific Examples described below.

EXAMPLE 1

1) Preparation of Crude Extract

Dried bacterial cells of Sphingomonas sp. MK 346 was placed in a 200-ml metal centrifugal tube (3.0 g each for 6 tubes), each tube was added with 100 ml of chloroform/methanol solution (2:1, v/v), and the content of each tube was homogenized for one minute. The homogenized mixture was then centrifuged using a high-speed centrifugal separator at 10,000 rpm, 4° C. for 20 minutes, the supernatant was removed to be pooled, and the residue was again subjected to the same extraction processes. The resultant residue was dried in air and 200 ml of chloroform/ethanol (1:3, v/v) was added to the dried reside. The mixture was refluxed at 80° C. for 1 hour for extraction and centrifuged at 4° C. for 20 minutes using a high-speed centrifugal separator at 10,000 rpm. The supernatant was removed and the residue was subjected to the same extraction processes. The supernatants obtained from such two-step extraction were combined and concentrated to thereby obtain a crude extract.

2) Chromatographic Purification of Glycosphingolipid

The crude extract was suspended in 20 ml of chloroform/methanol solution (1:3, v/v), and then purified by quarters (5 ml each) by column chromatography. Silica gel (Merck, 70 to 230 mesh) suspended in chloroform was packed into a column (2×12 cm), and 5 ml of the crude extract was placed thereon. Elution was then proceeded successively using 50 ml of chloroform/methanol solution (4:1, v/v), 50 ml of chloroform/methanol solution (2:1, v/v), 100 ml of chloroform/methanol solution (1:1, v/v) and 100 ml of chloroform/methanol (1:3, v/v). Eluted lipid was then examined by thin layer chromatography (TLC). That is, the lipids were developed on a 5×7.5 cm TLC plate (Merck, Silica Gel 60 F254) using chloroform/methanol/acetic acid/water mixed solution (25:15:4:2), and detected by spraying a 10% sulfuric acid/ethanol solution and by heating. Based on the result, fractions in which the target glycosphingolipid of an oligosaccharide type is supposed to be eluted were collected, and then evaporated to dryness under reduced pressure. The obtained solid was then dissolved in 10 ml of a 0.1 N NaOH solution, and kept at 80° C. for 2 hours on a water bath so as to proceed mild alkali treatment. The mixture was then neutralized with an 1 N HCl solution, dialyzed three times against water for 3 hours per run, and then lyophilized. The lyophilized glycosphingolipid was then chromatographed according to the foregoing conditions, and the obtained fractions of the glycosphingolipid were again evaporated to dryness under reduced pressure. The obtained sample was suspended in 0.5 ml of ethanol and 2 ml of water, the mixture was transferred into a dialysis tube, and dialyzed three times against the outer solution added with triethylamine (0.005%, pH 8 to 9) for 3 hours per run. The dialyzed solution was then lyophilized to thereby prepare a purified glycosphingolipid.

3) Determination of Fatty Acids

The purified glycosphingolipid (0.5 mg) was hydrolyzed in 4 N HCl (500 $\mu$l) at 100° C. for 5 hours, fatty acids were extracted from the hydrolysate, the extract was subjected to methyl-esterification using 5% HCl/methanol, and then analyzed by gas chromatography (GLC). A 25-m capillary column (CBP1, product of Shimadzu Corporation) was used for the GLC.

4) Analysis of Neutral Sugars

The purified glycosphingolipid (0.5 mg) was hydrolyzed in 0.1 N HCl (500 $\mu$l) at 100° C. for 48 hours, and the obtained neutral sugars were analyzed by GLC after being reduced with NaBH$_4$ into sugar alcohols and further acetylated. The Model CBP1 column was again used for the GLC.

5) Analysis of Glucosamines

The purified glycosphingolipid (0.5 mg) was hydrolyzed in 0.5 ml of 4 N HCl at 100° C. for 16 hours, and the obtained amino sugars were analyzed by GLC after being modified into the derivatives same as those for the neutral sugars. The Model CBP1 column was again used for the GLC.

6) Analysis of Compositional Ratio of Sphingosine

Four milligrams of the purified glycosphingolipid was suspended in 1 ml of water, added with 5 ml of 0.025 M NaIO$_4$, allowed to react under stirring at 4° C. for 5 days to thereby oxidize the sugar portion thereof. The oxidized product was lyophilized after being removed with the reagent, subjected to methanolysis in 1 ml of 1 N HCl/methanol at 100° C. for 5 hours, acetylated and analyzed by GLC. The Model CBP1 column was again used for the GLC.

7) Methylation Analysis of Glycosphingolipid

The glycosphingolipid (2 mg) was permethylated by Hakomori's method. The methylated glycosphingolipid was then hydrolyzed in 1 ml of 2 N or 1 N trifluoroacetic acid (TFA) at 120° C. for 2 hours. The hydrolysate was reduced with NaBH$_4$, the obtained partially methylated sugar alcohol was acetylated and then subjected to GLC analysis and gas chromatography/mass spectrometry (GC-MS) analysis.

8) Results of Compositional Analyses

The determination of fatty acids, neutral sugars and glucosamines composing the glycosphingolipid identified a molar ratio of 2-hydroxymyristic acid, mannose and glucosamine as 1:1.1:2.1. The analysis of the sphingosine revealed that a molar ratio of 2-amino-1,3-octadecanediol, 2-amino-13,14-methylene-1,3-eicosanediol and 2-amino-13-cicosene-1,3-diol as 1.9:1.0:0.1 (calculated based on ratio of the peak area).

9) Results of Methylation Analysis

The purified glycosphingolipid (2 mg) was N-acetylated, subjected to direct methylation, and carboxyl group of uronic acid unit were then reduced overnight using 1 ml of an 1:1 mixed solution of methanol and water containing 40 mg of NaBH$_4$. The product was then hydrolyzed, reduced and acetylated as described in the foregoing method 7), and analyzed by GC-MS analysis (EI-MS or CI-MS). Retention time of the sample was compared with those for the standard samples prepared using commercial sugar reagents. The analysis successfully identified 1,5-di-O-acetyl-2,3,4,6-tetra-O-methyl-annitol, 1,4,5,6-tetra-O-acetyl-2,3-di-O-methyl-glucitol, 1,5,6-tri-O-acetyl-2-deoxy-3,4-di-O-methyl-2-(N-methylacetamide)-glucitol, and 1,3,5-tri-O-acetyl-2-deoxy-4,6-di-O-methyl-2-(N-methylacetamide)-glucitol derivatives.

10) Results of Partially Degraded Products

The purified glycosphingolipid (1 mg) was hydrolyzed with 4 N HCl at 100° C. for 5 hours, disaccharides contained in the hydrolysate were then N-acetylated and reduced with NaBH$_4$, and subjected to GC-MS analysis after being methylated. The analysis revealed two kinds of disaccharide derivatives having a molecular weight of 526 and 553. One of which was identified based on an EI-MS spectrum as permethylated α-GlcNAc-(1→4)-GlcA-ol. The other derivative was identified also based on an EI-MS spectrum as permethylated β-GlcNAc-(1→6)-GlcNAc-ol.

11) Analyses by $^1$H- and $^{13}$C-NMR

Figure 1:
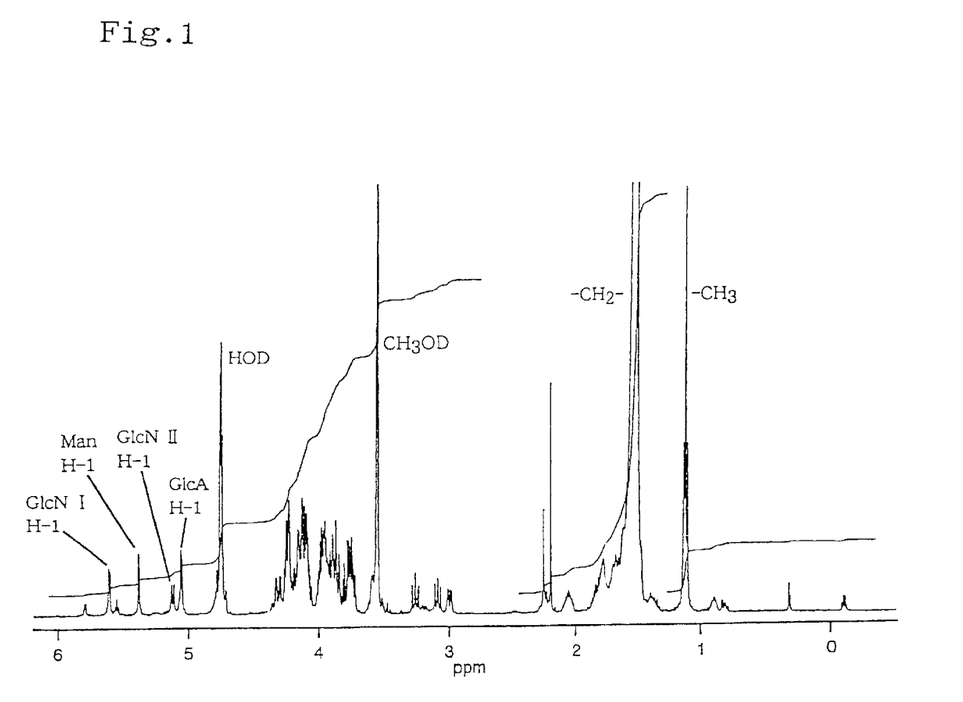
FIG. 1 is a chart showing $^1$H NMR spectrum of a pure glycosphingolipid obtained in Example 1.

A spectrum chart of $^1$H-NMR analysis of the purified glycosphingolipid was shown in FIG. 1 (CDCl$_3$:CD$_3$OD= 1:2 (v/v), 400 MHz, 45° C.). Four equivalent signals were observed at 5.0 ppm to 5.7 ppm in an anomer proton region (H-1), which suggested that the sugar chain has a tetrasaccharide structure. Assignments of the individual H-1 signals were estimated based on the previous data on other glycosphingolipid, and the chemical shifts and coupling constants thereof were measured (Table 1). Assignments of the individual C-1 signals were estimated from $^{13}$C— and $^1$H-COSY spectra, and chemical shifts and coupling constants of the C-1 signals for mannose and glucuronic acid were measured (Table 2). α-Mannose, α-glucosamine, β-glucosamine and α-glucuronic acid were thus identified.

TABLE 1

|  | Chemical shift (ppm) | Coupling constant (Hz) |
| --- | --- | --- |
| Glucuronic acid | 5.06 | 3.8 |
| Glucosamine I | 5.61 | 3.6 |
| Glucosamine II | 5.13 | 8.3 |
| Mannose | 5.39 | 2.0 |

TABLE 2

| | Chemical shift (ppm) | Coupling constant (Hz) |
|---|---|---|
| Glucuronic acid | 100.14 | 168.3 |
| Mannose | 102.85 | 171.0 |

It was confirmed from the above that the purified glycosphingolipid has a structure expressed by formula (I), where $R^1$ represents the sugar chain expressed by formula (A), $R^2$ represents any one of structures "a" to "c", and $R^3$ represents a straight alkyl group having a carbon number of 12.

Examples 2 to 21 described below employed the individual ingredients listed in Table 3 as the active ingredient of the glycosphingolipid expressed by formula (I). In all cases, $R^1$ in the glycosphingolipid contained in the active ingredient represents a sugar chain expressed by formula (A), and $R^3$ represents a straight alkyl group carbon number of 12.

TABLE 3

| Active Ingredient | $R^2$ | Part by weight |
|---|---|---|
| 1 | structure "a" | 1.00 |
| 2 | structure "b" | 1.00 |
| 3 | structure "c" | 1.00 |
| 4 | structure "a" | 0.50 |
|   | structure "b" | 0.50 |
| 5 | structure "a" | 0.50 |
|   | structure "c" | 0.50 |
| 6 | structure "b" | 0.50 |
|   | structure "c" | 0.50 |
| 7 | structure "a" | 0.34 |
|   | structure "b" | 0.33 |
|   | structure "c" | 0.33 |
| 8 | structure "a" | 0.64 |
|   | structure "b" | 0.03 |
|   | structure "c" | 0.33 |

EXAMPLE 2

Preparation of Beauty Skin Milk

A first solution obtained by mixing the individual components at 75° C. was added to a second solution obtained by mixing the individual components at 75° C., thoroughly emulsified at 75° C. to thereby prepare a beauty skin milk.

TABLE 4

| Ingredient | Part by weight |
|---|---|
| (First Solution) | |
| Squalane | 4.9 |
| Monostearic acid | 1.8 |
| Vaseline | 1.2 |
| Butyl paraben | 0.1 |
| Liquid paraffin | 5.0 |
| (Second Solution) | |
| Active ingredients listed in Table 3 | 1.0 |
| Sodium cetylsulfate | 0.8 |
| Methyl paraben | 0.2 |
| Purified water | 85.0 |

EXAMPLE 3

Preparation of Beauty Lotion

Various ingredients listed in table below were mixed at room temperature and thoroughly stirred to prepare a beauty lotion.

TABLE 5

| Ingredient | Part by weight |
|---|---|
| Active ingredients listed in Table 3 | 1.0 |
| Methylparaben | 0.1 |
| Polyoxyethylene hydrogenated castor oil | 1.2 |
| Polyoxyethylene sorbitan oleate | 0.4 |
| Ethanol | 5.3 |
| Purified water | 92.0 |

EXAMPLE 4

Preparation of Powder Foundation

Various ingredients listed in table below were mixed at room temperature and thoroughly stirred to prepare a powder foundation.

TABLE 6

| Ingredient | Part by weight |
|---|---|
| Active ingredients listed in Table 3 | 1.0 |
| Mica | 37.8 |
| Talc | 20.0 |
| Titanium dioxide | 12.0 |
| Kaolin | 5.0 |
| Iron oxide | 3.5 |
| Nylon powder | 8.0 |
| Octyldodecyl myristate | 2.0 |
| Neopentylglycol diisooctanoate | 2.0 |
| Sorbitan monooleate | 0.5 |
| Zinc stearate | 1.0 |
| Red oxide | 1.0 |
| Squalane | 6.0 |
| Preservative | 0.1 |
| Antioxidant | 0.1 |

EXAMPLE 5

Preparation of Whitening Powder

Various ingredients listed in table below were mixed and pulverized at room temperature to prepare a whitening powder.

TABLE 7

| Ingredient | Part by weight |
|---|---|
| Active ingredients listed in Table 3 | 20.0 |
| Sucrose | 50.0 |
| Polyethylene glycol | 10.0 |
| Silica | 4.5 |
| Vitamin C | 5.0 |
| Vitamin C dipalmitate | 10.0 |
| Dye | 0.5 |

EXAMPLE 6

Preparation of Emollient Cream 1,3-Butylene glycol and purified water listed in table below were mixed and heated to 70° C., a mixture of the residual ingredients molten by heating was added thereto, the mixture was emulsified and homogenized using a homimixer, and the emulsion was cooled to prepare a emollient cream.

TABLE 8

| Ingredient | Part by weight |
| --- | --- |
| Active ingredients listed in Table 3 | 5.0 |
| Stearyl alcohol | 6.0 |
| Stearic acid | 2.0 |
| Hydrogenated lanolin | 4.0 |
| Squalane | 9.0 |
| Octyl dodecanol | 10.0 |
| POE (25) cetyl alcohol ether | 3.0 |
| Glycerin monostearate | 2.0 |
| 1,3-Butylene glycol | 10.0 |
| Dye | 0.5 |
| Preservative | 0.1 |
| Antioxidant | 0.1 |
| Purified water | 48.3 |

EXAMPLE 7

Preparation of Pre-shaving Lotion

Various ingredients listed in table below were mixed at room temperature, and thoroughly stirred to prepare a pre-shaving lotion.

TABLE 9

| Ingredient | Part by weight |
| --- | --- |
| Active ingredients listed in Table 3 | 1.0 |
| Zinc phenol sulfonate | 1.0 |
| Isopropylmyristate ester | 7.0 |
| Isopropylpalmitate ester | 8.0 |
| Ethanol | 82.5 |
| Perfume | 0.5 |

EXAMPLE 8

Preparation of Cleansing Foam

Stearic acid, palmitic acid, myristic acid, lauric acid, coconut oil and preservative listed in table below were molten by heating and kept at 70° C. and a mixture of potassium hydroxide and purified water was added under stirring. Then, the residual ingredients were added thereto, the mixture was thoroughly stirred, and then deaerated and cooled to prepare a cleansing foam.

TABLE 10

| Ingredient | Part by weight |
| --- | --- |
| Active ingredients listed in Table 3 | 4.5 |
| Stearic acid | 10.0 |
| Palmitic acid | 10.0 |
| Myristic acid | 12.0 |
| Lauric acid | 4.0 |
| Coconut oil | 2.0 |
| Potassium hydroxide | 6.0 |
| Glycerol monostearate ester | 2.0 |
| POE (25) sorbitan monostearate | 2.0 |
| Dye | 0.5 |
| Preservative | 0.1 |
| Chelating agent | 0.2 |
| Purified water | 46.7 |

EXAMPLE 9

Preparation of Pack

Titanium oxide and talc listed in table below were thoroughly dispersed in purified water and then combined with sorbitol. The mixture was molten by heating to 70° C. and added with the residual ingredients, the mixture was thoroughly stirred, deaerated and cooled to prepare a pack.

TABLE 11

| Ingredient | Part by weight |
| --- | --- |
| Active ingredients listed in Table 3 | 4.5 |
| Polyvinyl acetate emulsion | 15.0 |
| Polyvinyl alcohol | 10.0 |
| Jojoba oil | 2.0 |
| Squalane | 2.0 |
| POE sorbitan monostearate ester | 1.0 |
| Titanium oxide | 5.0 |
| Talc | 10.0 |
| Sorbitol | 10.0 |
| Ethanol | 8.0 |
| Dye | 0.5 |
| Preservative | 0.2 |
| Purified water | 31.8 |

EXAMPLE 10

Preparation of Lipstick

Various ingredients listed in table below were heated to 70° C. and then mixed. The mixture was thoroughly stirred, cast and then rapidly cooled to prepare a lipstick.

TABLE 12

| Ingredient | Part by weight |
| --- | --- |
| Active ingredients listed in Table 3 | 2.0 |
| Castor oil | 25.0 |
| Cetyl 2-ethylhexanoate | 20.0 |
| Lanolin | 10.0 |
| Isopropyl myristate ester | 10.0 |
| Candelilla wax | 9.0 |
| Solid paraffin | 8.0 |
| Carnauba wax | 5.0 |
| Beeswax | 5.0 |
| Titanium dioxide | 5.0 |
| Dye | 1.0 |

EXAMPLE 11

Preparation of Lip Cream

Active ingredients, stearic acid, stearyl alcohol and butyl stearate listed in table below were heated to 70° C. and then mixed, and further added with a mixture of the residual ingredients. The mixture was thoroughly stirred to prepare a lip cream.

TABLE 13

| Ingredient | Part by weight |
| --- | --- |
| Active ingredients listed in Table 3 | 4.0 |
| Stearic acid | 14.0 |
| Stearyl alcohol | 8.0 |
| Butyl stearate | 10.0 |
| Propylene glycol | 10.0 |
| Glycerin monostearate | 4.0 |
| Potassium hydroxide | 1.0 |
| Antioxidant | 0.2 |
| Purified water | 48.8 |

EXAMPLE 12

Preparation of Cheek Color

Various ingredients except for perfume and liquid paraffin listed in table below were mixed at room temperature and then sprayed with perfume and liquid paraffin and pulverized. The mixture was compression molded to prepare a cheek color.

TABLE 14

| Ingredient | Part by weight |
| --- | --- |
| Active ingredients listed in Table 3 | 1.5 |
| Talc | 77.8 |
| Kaolin | 9.0 |
| Zinc myristate | 5.0 |
| Pigment | 3.0 |
| Liquid paraffin | 3.0 |
| Perfume | 0.5 |
| Preservative | 0.2 |

EXAMPLE 13

Preparation of Eyeliner

Carbon black listed in table below was pulverized and then dispersed in purified water, and the residual ingredients were mixed at room temperature to prepare an eyeliner.

TABLE 15

| Ingredient | Part by weight |
| --- | --- |
| Active ingredients listed in Table 3 | 10.0 |
| Carbon black | 5.0 |
| Polyoxyethylene dodecyl ether | 2.0 |
| Dye | 0.5 |
| Preservative | 0.2 |
| Purified water | 82.3 |

EXAMPLE 14

Preparation of Mascara

Iron oxide, purified water and polyacrylate ester emulsion listed in table below were mixed at 70° C. and combined with a mixture of the residual ingredients molten by heating to 70° C. The mixture was dispersed by emulsification to prepare a mascara.

TABLE 16

| Ingredient | Part by weight |
| --- | --- |
| Active ingredients listed in Table 3 | 4.5 |
| Iron oxide | 10.0 |
| Polyacrylate ester emulsion | 27.0 |
| Solid paraffin | 8.0 |
| Lanolin wax | 8.0 |
| Light isoparaffin | 28.0 |
| Sorbitan sesquioleate | 4.0 |
| Dye | 0.5 |
| Antioxidant | 0.1 |
| Preservative | 0.1 |
| Purified water | 9.8 |

EXAMPLE 15

Preparation of Eyebrow Color

Various ingredients except for powdery ingredients listed in table below were molten and mixed, and then added with powdery ingredients. The mixture was kneaded and molded to prepare an eyebrow color.

TABLE 17

| Ingredient | Part by weight |
| --- | --- |
| Active ingredients listed in Table 3 | 1.0 |
| Iron oxide | 19.0 |
| Titanium oxide | 5.0 |
| Talc | 10.0 |
| Kaolin | 15.0 |
| Japan wax | 20.0 |
| Stearic acid | 10.0 |
| Beeswax | 5.0 |
| Hydrogenated castor oil | 5.0 |
| Vaseline | 4.0 |
| Lanolin | 3.0 |
| Liquid paraffin | 2.8 |
| Antioxidant | 0.1 |
| Preservative | 0.1 |

EXAMPLE 16

Preparation of Hand Cream

Various ingredients listed in table below were mixed under heating at 70° C. and thoroughly stirred to prepare a hand cream.

TABLE 18

| Ingredient | Part by weight |
| --- | --- |
| Active ingredients listed in Table 3 | 3.0 |
| Glycerin | 20.0 |
| Urea | 2.0 |
| Monoglyceride stearate | 2.5 |
| Vaseline | 6.0 |
| Liquid paraffin | 10.0 |
| Purified water | 56.5 |

EXAMPLE 17

Preparation of Hair Shampoo

Various ingredients listed in table below were mixed under heating at 70° C. and thoroughly stirred to prepare a hair shampoo.

TABLE 19

| Ingredient | Part by weight |
|---|---|
| Active ingredients listed in Table 3 | 5.0 |
| Glycerin | 1.0 |
| Sodium polyoxyethylene lauryl sulfate ester | 10.0 |
| Sodium lauryl sulfate ester | 6.0 |
| Coconut fatty acid diethanolamide | 3.0 |
| Sequestrant | 0.1 |
| pH modulator | 0.5 |
| Preservative | 0.2 |
| Purified water | 74.2 |

EXAMPLE 18

Preparation of Hair Rinse

Various ingredients listed in table below were mixed under heating at 70° C. and thoroughly stirred to prepare a hair rinse.

TABLE 20

| Ingredient | Part by weight |
|---|---|
| Active ingredients listed in Table 3 | 3.0 |
| Silicone oil | 2.8 |
| Liquid paraffin | 1.2 |
| Glycerin | 2.5 |
| Cetyl alcohol | 1.3 |
| Stearyl alcohol | 1.1 |
| Stearyltrimethylammonium chloride | 0.6 |
| Dye | 1.0 |
| Preservative | 0.2 |
| Purified water | 86.3 |

EXAMPLE 19

Preparation of Hair Lotion

Various ingredients listed in table below were mixed at room temperature to prepare a hair lotion.

TABLE 21

| Ingredient | Part by weight |
|---|---|
| Active ingredients listed in Table 3 | 1.0 |
| Polyoxypropylene butyl ether | 20.0 |
| Polyoxyethylene hydrogenated castor oil | 1.0 |
| Ethanol | 50.0 |
| Perfume | 0.5 |
| Purified water | 27.5 |

EXAMPLE 20

Preparation of Hair Dye

Various ingredients listed in table below were mixed at room temperature to prepare a hair dye.

TABLE 22

| Ingredient | Part by weight |
|---|---|
| Active ingredients listed in Table 3 | 3.0 |
| Pigment | 1.0 |
| Acryl resin alkanolamine (50%) | 8.0 |

TABLE 22-continued

| Ingredient | Part by weight |
|---|---|
| Perfume | 0.5 |
| Ethanol | 88.0 |

EXAMPLE 21

Preparation of Bath Formula

Various ingredients listed in table below were mixed at room temperature to prepare a bath formula.

TABLE 23

| Ingredient | Part by weight |
|---|---|
| Active ingredients listed in Table 3 | 10 |
| Sodium sulfate | 50 |
| Sodium hydrogencarbonate | 25 |
| Sodium chloride | 13 |
| Dye | 2 |

As has been described in the above, the present invention provides a novel glycosphingolipid having a sugar chain containing α-glucosamine and β-glucosamine. Such glycosphingolipid of the present invention is advantageous in that possibly being manufactured in a facile and inexpensive manner, and that exhibiting moisturizing effect and immuno-enhancing activity.

What is claimed is:

1. A glycosphingolipid having a sugar chain containing α-glucosamine and β-glucosamine.

2. The glycosphingolipid as claimed in claim 1, wherein said sugar chain comprises a mannose, a β-glucosamine, an α-glucosamine and a glucuronic acid.

3. The glycosphingolipid as claimed in claim 2, wherein said sugar chain has a structure expressed by formula (A) below:

$$\alpha\text{-Man-}(1\rightarrow3)\text{-}\beta\text{-GlcN-}(1\rightarrow6)\text{-}\alpha\text{-GlcN-}(1\rightarrow4)\text{-}\alpha\text{-GlcA-} \quad (A)$$

wherein Man represents mannose, GlcN represents glucosamine and GlcA represents glucuronic acid.

4. The glycosphingolipid as claimed in claim 1 having a structure expressed by the formula below:

(I)

wherein $R^1$ represents said sugar chain containing an α-glucosamine and an β-glucosamine, $R^2$ represents any one of an alkyl group possibly having cycloalkyl group, an alkenyl group and an alkynyl group; $R^3$ represents an alkyl group; all of such alkyl group, alkenyl group and alkynyl group may be straight or branched, and may be substituted or unsubstituted.

5. The glycosphingolipid as claimed in claim 4, wherein said $R^2$ has a carbon number of 15 to 25.

6. The glycosphingolipid as claimed in claim 5, wherein said $R^2$ has a structure expressed by any one of the formulae below:

7. The glycosphingolipid as claimed in claim 4, wherein said $R^3$ is a substituted or unsubstituted straight alkyl group having a carbon number of 10 to 20.

8. The glycosphingolipid as claimed in claim 7, wherein said $R^3$ is a straight alkyl group having a carbon number of 12.

9. In a cosmetic containing a cosmetically acceptable adjuvant material, the improvement wherein said cosmetic further contains the glycosphingolipid as claimed in claim 1.

10. A pharmaceutical composition containing the glycosphingolipid as claimed in claim 1 and at least one of a pharmaceutically acceptable carrier and a pharmaceutically active agent.

11. In a moisturizer containing a cosmetically acceptable carrier material, the improvement wherein said moisturizer further contains the glycosphingolipid as claimed in claim 1.

* * * * *